United States Patent [19]

Barnes et al.

[11] Patent Number: 5,406,952
[45] Date of Patent: Apr. 18, 1995

[54] BLOOD PRESSURE MONITORING SYSTEM

[75] Inventors: Jeffrey T. Barnes, Norwood; J. Erik Moore, Charlestown, both of Mass.

[73] Assignee: Biosyss Corporation, Braintree, Mass.

[21] Appl. No.: 16,435

[22] Filed: Feb. 11, 1993

[51] Int. Cl.⁶ ............................................... A61B 5/00
[52] U.S. Cl. ..................................... 128/672; 128/687; 128/690; 364/413.03
[58] Field of Search ........................ 128/672, 677–687, 128/690; 364/413.03

[56] References Cited

U.S. PATENT DOCUMENTS

| | | | |
|---|---|---|---|
| 4,030,484 | 6/1977 | Kuska et al. | 128/2.05 R |
| 4,331,154 | 5/1982 | Broadwater et al. | 128/677 |
| 4,561,447 | 12/1985 | Kawamura et al. | 128/687 |
| 4,859,057 | 8/1989 | Taylor et al. | 128/633 |
| 4,960,128 | 10/1990 | Gordon et al. | 128/677 |
| 5,033,471 | 7/1991 | Yokoe et al. | 128/681 |
| 5,099,852 | 3/1992 | Meister et al. | 128/672 |
| 5,099,853 | 3/1992 | Uemera et al. | 128/681 |
| 5,099,854 | 3/1992 | Choi | 128/690 |
| 5,101,829 | 4/1992 | Fujikawa et al. | 128/672 |
| 5,109,863 | 5/1992 | Semmlow et al. | 128/715 |
| 5,140,991 | 8/1992 | Niwa | 128/687 |

FOREIGN PATENT DOCUMENTS

| | | |
|---|---|---|
| 0347515 | 12/1989 | Belgium . |
| 0482242A1 | 4/1992 | European Pat. Off. . |
| WO93/04625 | 3/1993 | European Pat. Off. . |
| 2118791 | 7/1992 | United Kingdom . |
| WO92/06633 | 4/1992 | WIPO . |
| WO92/07508 | 5/1992 | WIPO . |
| WO92/11804 | 7/1992 | WIPO . |

Primary Examiner—Kyle L. Howell
Assistant Examiner—Robert L. Nasser, Jr.
Attorney, Agent, or Firm—Hamilton, Brook, Smith & Reynolds

[57] ABSTRACT

A blood pressure instrument and method in which analog blood pressure waveform signals are digitized and stored and used to determine blood pressure parameters to make physiological measurements based upon pattern recognition using information empirically obtained from clinical measurements. In a preferred embodiment, the analog waveform signals are obtained non-invasively using an external wrist-mounted displacement transducer.

22 Claims, 5 Drawing Sheets

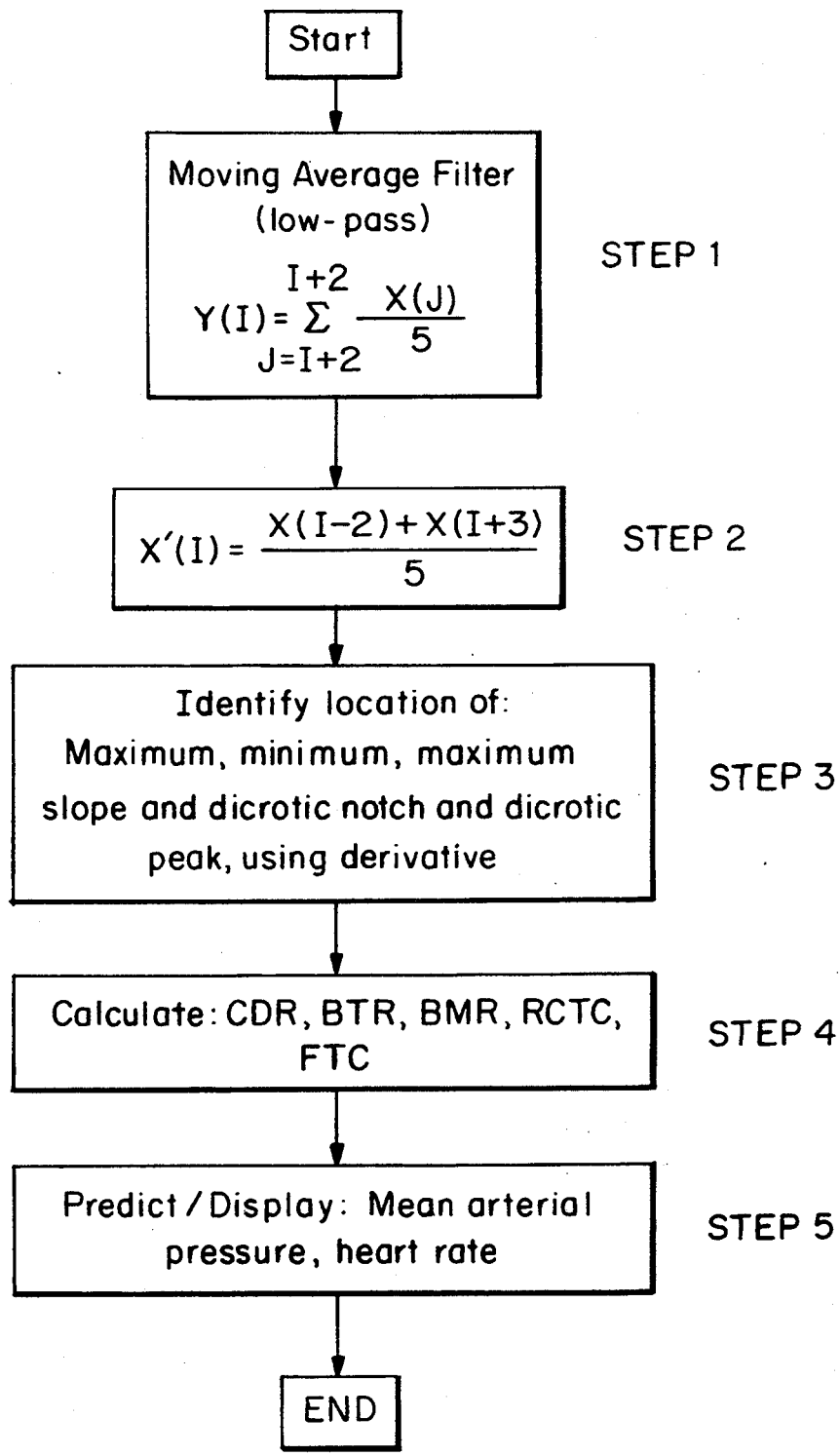

BLOOD PRESSURE MONITORING SYSTEM

BACKGROUND OF THE INVENTION

This invention relates to devices and methods for continuously and non-invasively measuring arterial blood pressure and heart rate.

Physiological measurement of blood pressure provides important diagnostic information to medical practitioners regarding the state of the patient's circulatory and cardiac systems. Techniques for measuring arterial pressure include invasive and non-invasive methods, each including an assortment of apparatus and techniques. A typical invasive technique includes inserting a catheter directly into the artery to be monitored, and measuring the pressure induced on a column of fluid within the catheter with an external pressure transducer.

Non-invasive techniques for measuring arterial pressure include an assortment of apparatus and techniques including intermittent occlusive and continuous non-occlusive techniques.

SUMMARY OF THE INVENTION

The present invention provides a device and method for continuously and non-invasively measuring arterial blood pressure and heart rate. The device offers the advantages of simply coupling a transducer to a person's wrist to provide a real-time blood pressure monitoring system. Advantageously, the device operates non-invasively and without occlusion. Electrical signals generated by the device can be used to derive mean blood pressure and heart rate measurements. The device produces waveforms similar to those produced by invasive monitoring techniques. These waveform morphologies provide a convenient means for deriving a wide variety of blood pressure and heart beat parameters.

In accordance with the invention a non-invasive device is provided which attaches to the wrist of the patient and generates electrical signals in response to arterial pulses. A signal conditioning apparatus is connected to the wrist device to analyze these electrical signals and to derive values for mean blood pressure, and heart rate. Measurements of these parameters are made on substantially every arterial pulse to provide a substantially real-time blood pressure monitoring system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 6 is a flowchart diagramming the "Beat Evaluation" process for extracting blood pressure parameters and making physiological measurements from the waveform of FIG. 4 by the electronic processing system of FIG. 1.

DESCRIPTION OF THE PREFERRED EMBODIMENT

Figure 1:
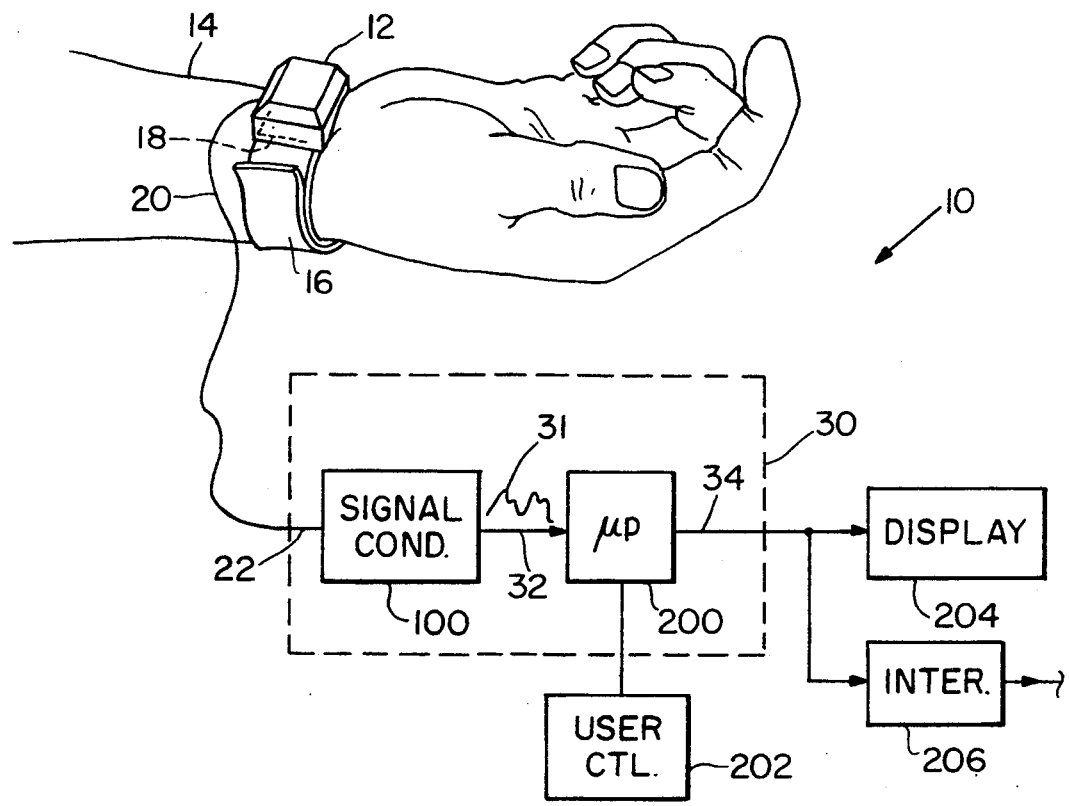
FIG. 1 shows a schematic block diagram of the non-invasive blood pressure measurement and monitoring system of this invention, including a strap-on wrist transducer and electronic processing apparatus.

FIG. 1 shows a preferred embodiment of a non-invasive blood pressure measurement and monitoring system 10 of this invention. Blood pressure measurement system 10 includes a piezoelectric displacement transducer 12 configured for attachment to a patient's wrist 14 with an adjustable wrist strap 16. A foam pad 18 having an adhesive surface 18(a) and 18(b) (See FIG. 2) is applied to the underside of transducer 12 to enable transducer 12 to be removably adhered to the patient's wrist. The contact portion of transducer 12 is placed directly over the patient's radial artery in a manner that causes displacement of the transducer element in response to displacement of the radial artery caused by blood pressure pulses. The result is that the electrical signal output from the piezoelectric transducer is indicative of the radial arterial displacement. Adjustable wrist strap 16, which can include an elastic band, a plurality of snaps, or a velcro type fastener, aids in maintaining contact between transducer 12 and the surface of the wrist directly above the radial artery.

The electrical output signal of piezoelectric displacement transducer 12 is connected by an electrical signal cable 20 to the input 22 of a signal processing apparatus 30. Signal processing apparatus 30 includes a signal conditioner 100 which receives the output of the displacement transducer 12 and processes the displacement signal to produce an analog blood pressure waveform 31 at its output 32. The blood pressure waveform signal output from signal conditioner 100 is input to a microprocessor/digital signal processor 200. Microprocessor/digital signal processor 200 accepts commands from a user control interface 202 and processes the blood pressure waveform to extract various parameters and make physiological measurements. The processed blood pressure waveforms, extracted parameters, and physiological measurements are output from the microprocessor 200 for display on a display device 204, which can include a CRT, chart recorder, a liquid crystal display, or any other commonly available means for displaying computer generated data and waveforms. Furthermore, the waveforms, parameters, and measurements can be sent through an instrument interface 206 for coupling to other medical instruments or data processing devices.

Figure 2:
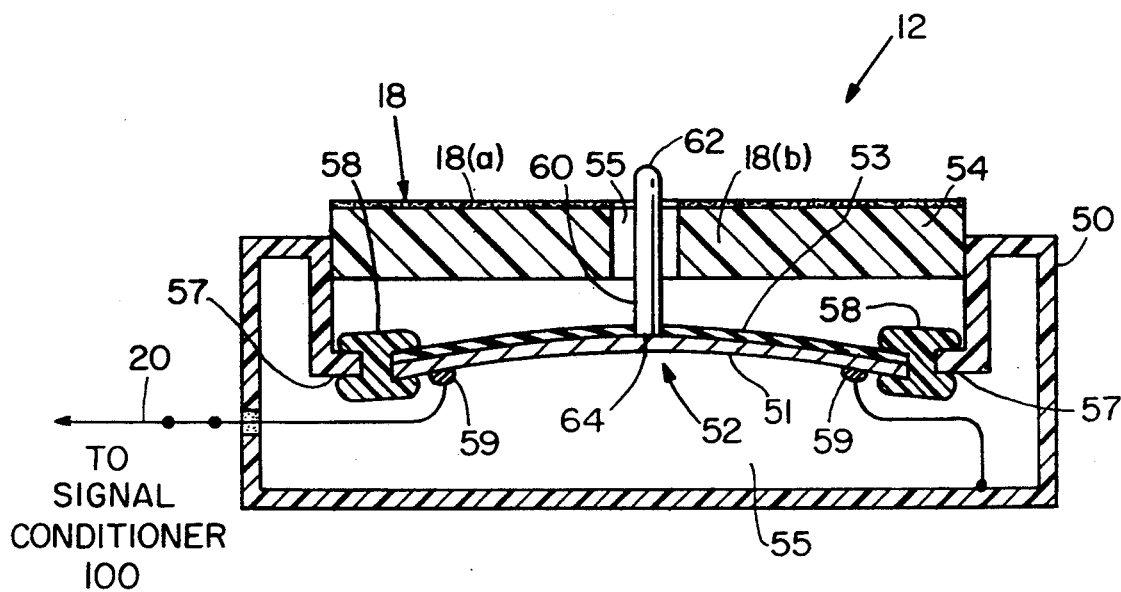
FIG. 2 is a cross-section representation of the piezoceramic wrist transducer of the blood pressure measurement and monitoring system of FIG. 1.

FIG. 2 shows a cross-sectional view of the piezoelectric displacement transducer 12 of FIG. 1. Transducer 12 includes a plastic housing 50 encasing an electromechanical piezoceramic sensing element 52. Plastic housing 50 includes a raised plastic annular disk 54, having a central aperture 55, for enclosing the top of the transducer. A disposable, double-backed, adhesive foam pad 18 conforming to the shape of plastic disk 54 is adapted to adhere on one side to plastic disk 54 and on the other side to a patient's wrist. Pad 18 acts as a mounting pad for coupling the transducer to the wrist and helps to eliminate noise artifacts due to wrist movement. The pad also provides a comfortable interface between the plastic transducer housing and the patient's wrist. The foam pad also contains an adhesive 18(a) and 18(b) on both sides which serves to prevent lateral movement of the transducer thus ensuring adequate signal strength. The foam pad is also designed to be removed and replaced with a new one after each blood pressure measurement procedure.

Electro-mechanical sensing element 52 is a composite constructed from a 10 mil thick layer of piezoceramic 53 bonded to a 10 mil thick brass disk 51. This composite structure provides an optimal modulus of elasticity for the strain coefficient of the ceramic to provide sufficient dynamic range with a good signal to noise ratio. Electrodes 59 are formed by nickel plating through electrolysis to provide electrical connections to the piezoceramic element. A strong direct current polarization produces the piezoelectric properties.

Electro-mechanical sensing element 52 is suspended around its circumference by a silicon rubber ring 58 placed between the sensing element 52 and an annular step 57 formed in the plastic housing 50. A vertical displacement transfer member 60 has one end 62 extending through the central aperture 55 of plastic disk 54 for contacting the patient's wrist directly above the radial artery, and another end 64 attached to the center of the composite piezoceramic transducer disk 52. This arrangement allows the composite disk 52 to flex vertically in response to the forces applied to the displacement member from arterial displacement. The composite disk is thus suspended so that displacement of the radial artery translates into flexing of the composite disc, which generates an electrical signal related to displacement of the radial artery.

An adjustable strap is employed to secure the transducer and housing around the wrist to maintain transducer pressure over the radial artery in the wrist. The piezoceramic material of the transducer element 52 is AC coupled to the input of signal conditioner 100 (FIG. 1) due to the capacitive characteristic of the transducer element. Thus, any DC component of the generated displacement signal caused by the static pressure of the transducer against the wrist is eliminated. Therefore, the amount of static transducer pressure created by the securing strap or changes in the wrist-hand position will not affect the steady-state performance of the blood pressure measurement and monitoring system. Furthermore, performance is enhanced since the pressure derivation methods discussed below function independently of signal amplitude. It is important to note that no direct pressure measurements are being made, since the sensor measures displacement and not pressure.

The output of the piezoceramic sensing element 52 appears as an AC coupled displacement signal due to the capacitive and resistive characteristics of the sensing element.

Specific waveform patterns, or morphologies, of the displacement signal can be analyzed to determine blood pressure values. Since the analysis system of this invention is based on pattern recognition and morphology analysis, and not absolute signal amplitude, there is no need to employ a calibrated pressure transducer. Furthermore, the absolute amplitude of the displacement signal obtained with the piezoceramic transducer of this invention is relatively unimportant and thus specific dimensions (e.g., volts, mmHg, etc.) are not required for the purposes of signal processing or the application of blood pressure measurement methods.

Figure 3:
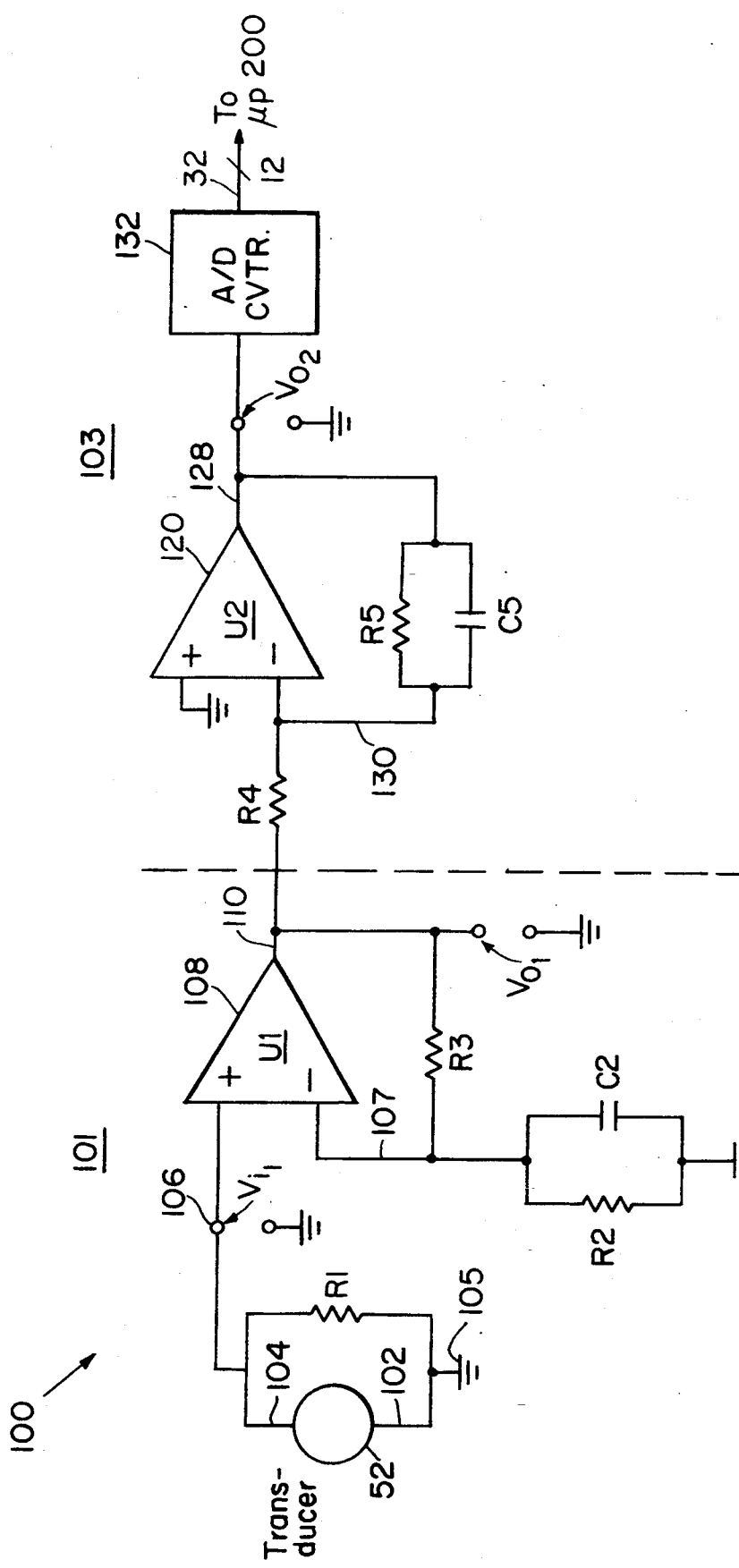
FIG. 3 is a schematic circuit diagram for the signal conditioning portion of the electronic processing apparatus of the blood pressure measurement and monitoring system of FIG. 1.

FIG. 3 is a schematic diagram of the signal conditioning circuit 100 of the blood pressure signal processing apparatus 30 of FIG. 1.

Conditioning circuit 100 includes two processing stages, an input amplifier stage 101 and a low-pass stage 103 (shown in dotted lines). Input amplifier stage 101 provides impedance matching and amplification for piezoceramic displacement transducer 52 by means of an operational (Op) amplifier 108 and its corresponding circuitry. Op amp 108 is employed in a non-inverting configuration yielding an input impedance greater than 100 megohms. The piezoceramic transducer element 52 has one electrode 102 connected to signal ground 105 and the other electrode 104 connected to the non-inverting input 106 of the operational amplifier 108. Transducer element 52 is also shunted to ground by a 100MΩ resistor R1 which acts in conjunction with the transducer element inherent capacitance to provide a sufficiently large time constant for the system. Transducer element 52 acts as a low current voltage source in response to the deformation of the piezoceramic transducer element by deflection of the radial artery. The shunt resistor R1 and the piezoceramic material of transducer 52 essentially form a first order high pass filter with a corner frequency determined by the values of the shunt resistor and the capacitance inherent to the transducer element.

The transfer function of the first amplifier stage in the frequency range of interest is approximately given by:

$$\frac{V_{o1}}{V_{i1}} = 1 + \frac{R3}{R2}$$

where $V_{o1}$ is the output voltage measured at amplifier output lead 110, $V_{i1}$ is the input voltage measured at input lead 106. R3 is a feedback resistor connected between amplifier output 110 and inverting input 107. R2 is a resistor connected in parallel with a capacitor C2. The parallel combination is connected between the inverting input 107 of the amplifier 108 and ground. With the selected values of R2 and R3 equal to 10KΩ each, and C2 equal to 0.001 μF, this transfer function provides a constant gain of approximately 2 over the desired frequency range of use. (This transfer function however does not take into account the zero formed by R2 and C2).

The output 110 of input amplifier stage 101 is input to the low pass filter stage 103 formed by another operational amplifier 120, an input resistor R4, and a parallel combination of resistor R5 and capacitor C5 connected between the output 128 of amplifier 120 and the inverting input 130 in a one pole low pass filter configuration. The filter operates on the amplified output of the transducer, which is the high pass filtered arterial wall displacement waveform. The transfer function of the filter is:

$$V_{o2}/V_{o1} = -\left(\frac{R5}{R4}\right)/(C5R5jw + 1)$$

where $V_{o2}$ is the output of amplifier 120 and $v_{o1}$ is the input of amplifier 120.

This circuit provides a low pass filter with a corner frequency in the range of 30–38 Hz and, preferably, approximately 34 Hz followed by a 20 dB per decade decrease in magnitude with increasing frequency. The overall gain of this stage of the circuit in the pass band is approximately $-1$. The total transfer function for the input amplifier circuit 101 and the low-pass filter circuit 103 is given by:

$$\frac{V_{o2}}{V_{i1}} = -\frac{\left(\frac{R5}{R4}\right)\left(1 + \frac{R3}{R4} + R3C2j\omega\right)}{1 + R5C5j\omega}$$

Therefore, the total transfer function for signal conditioning circuit 100 has a gain of $-2$ for frequencies less than 34 Hz and a 20 dB per decade attenuation for frequencies greater than 34 Hz. In this manner, interference predominantly from 60 Hz line voltage is minimized. Note that very little blood pressure information is contained in signals above 30 Hz in frequency.

The analog signal output from the signal conditioning circuit is digitized using a successive approximation analog digital converter 132 having 12 bits of resolution and a 120 Hz sampling rate. The 12 bit digital values are sent on lines 32 to micro processor/signal processor 200 where they are stored as 16 bit data words in successive locations of memory, each data word being representative of an analog voltage sample. The time spacing between samples is approximately 8 milliseconds.

Figure 4:
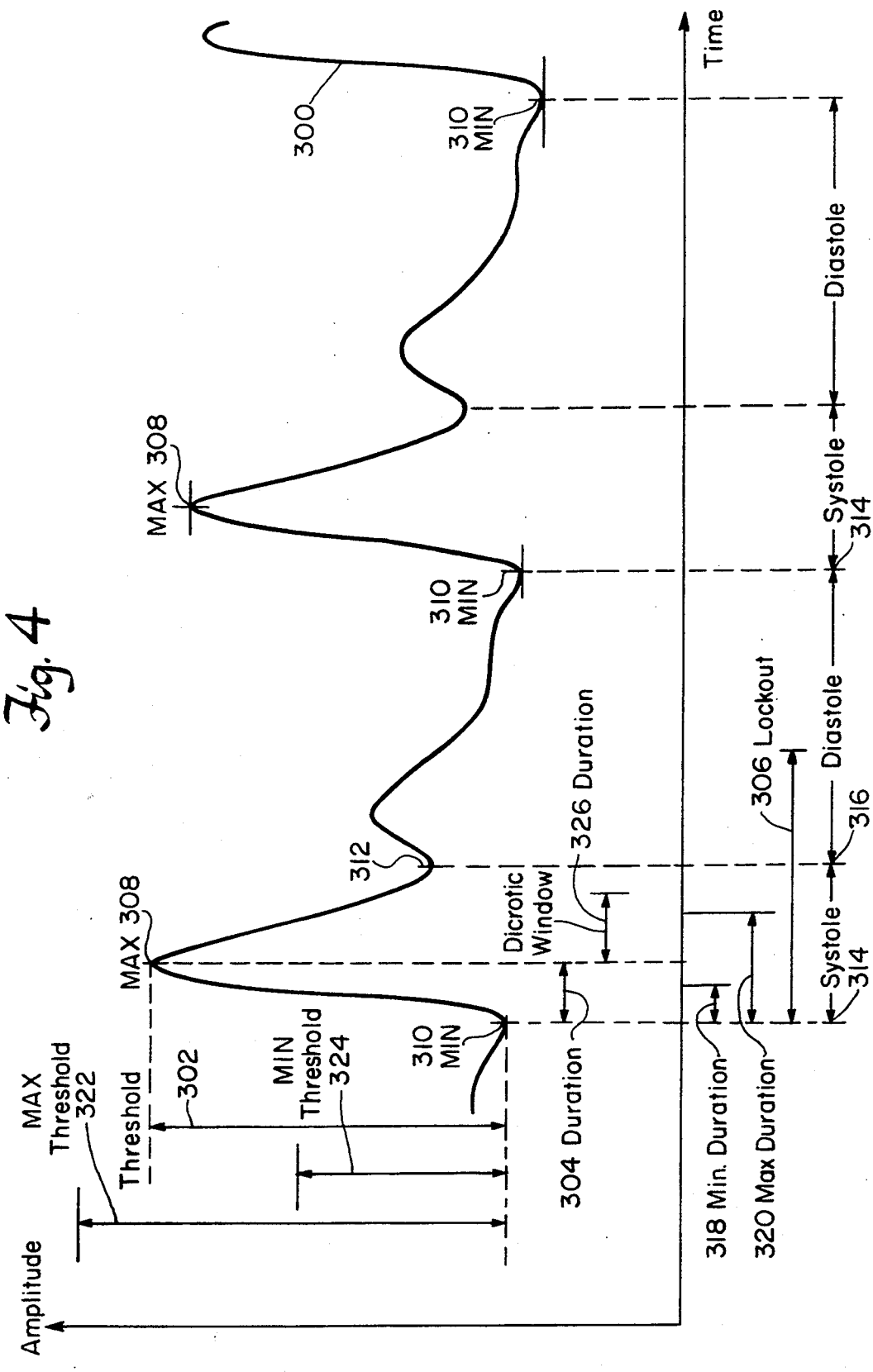
FIG. 4 is a waveform diagram showing the blood pressure waveform morphology produced by the electronic processing system of the blood pressure measuring and monitoring system of FIG. 1.

FIG. 4 shows a typical waveform output on line 128 from signal conditioning circuit 100 (FIG. 3). Microprocessor/signal processor 200 is programmed to perform a "beat detection" process on the waveform of FIG. 4 to discriminate valid blood pressure beat waveforms from invalid waveforms. A set of waveform specific parameters are developed and applied to the waveform signals to isolate and restrict different characteristics of the waveform and perform the beat detection process.

Figure 5:
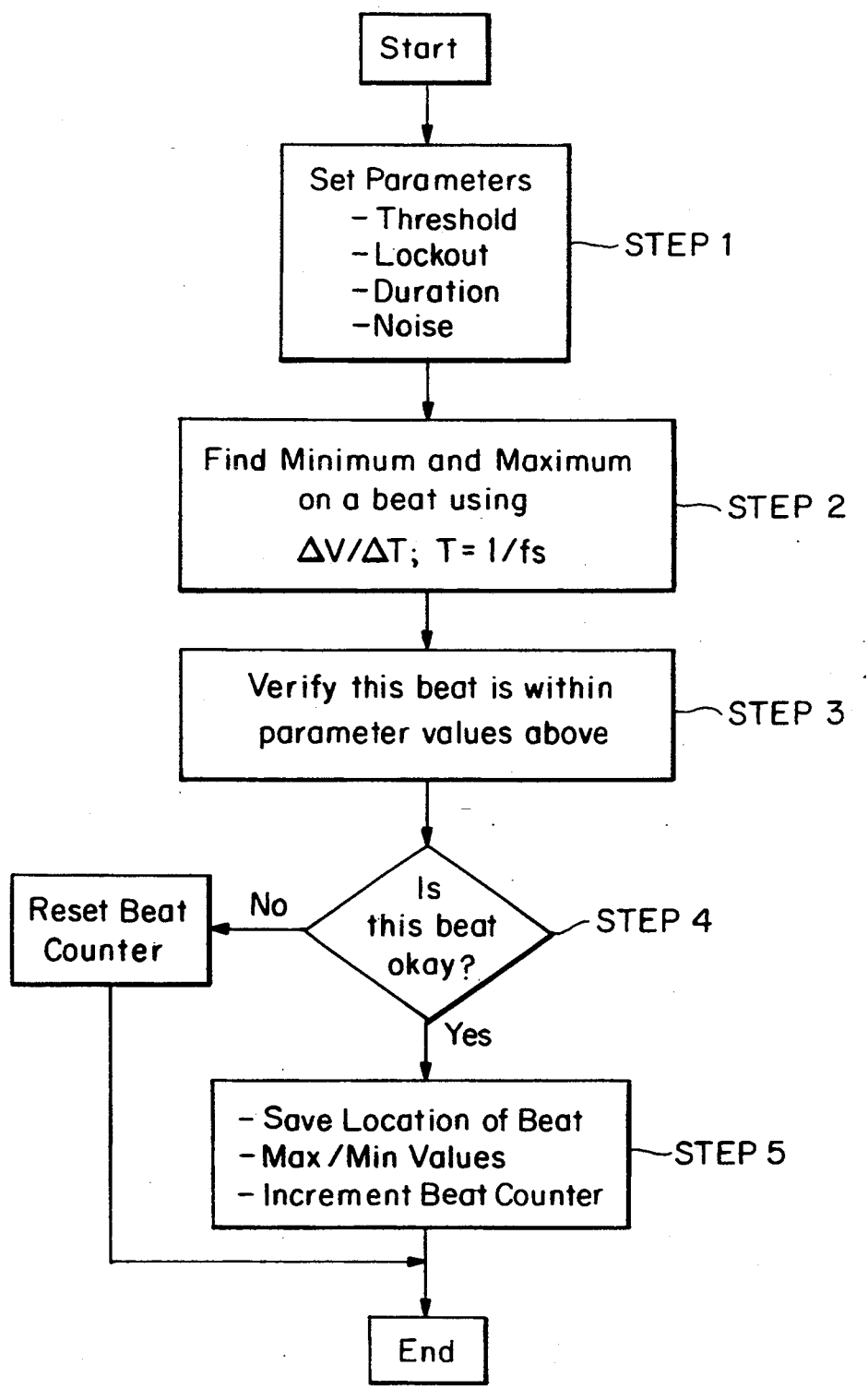
FIG. 5 is a flowchart diagramming the "Beat Detection" process for detecting valid beats performed on the waveform of FIG. 4 by the electronic processing system of FIG. 1.

FIG. 5 shows a flowchart diagram of the "beat detection" method of this invention for detecting valid blood pressure beats from the waveform 300 of FIG. 4. Once the digitized waveform data is stored in the memory of microprocessor/signal processor 200, the beat detection process begins by determining a set of parameters from the waveform data (Step 1). These parameters are determined by taking measurements of the waveform data and include a beat "threshold" 302 measurement, a beat "duration" 304 measurement, a beat "lockout" 306 measurement and a "noise level" measurement. These measurements are tested against a set of established parameters to identify valid beats (Step 3). "Threshold" is a measurement of the height of the beat waveform and is determined by finding the absolute maximum 308 and minimum 310 amplitude measurement for each beat. The beat waveform minimum value 310 and maximum value 308 are located by determining the difference in voltage magnitude $\Delta V$ between successive data points in time $\Delta T$. The length of time ($\Delta T$) between two samples is the reciprocal of the sampling rate $f_s$ (Step 2). For example, in a region where the magnitude is increasing, the point where the magnitude peaks and then decreases is defined as the maximum amplitude of the beat 308. Analogously, in a region where the magnitude is decreasing, the point where the magnitude has a minimum and then increases is defined as the minimum amplitude 310 of the beat.

Since the waveform data samples may be noisy and not strictly monotonic, it is possible that although the magnitude of the data points as a whole are for instance increasing, there may be regions where the magnitude decreases. It is necessary that the maxima preceding these small decreases in magnitude not be identified as the maximum amplitude 308 of the beat. The maxima preceding any decrease in magnitude is identified as a relative maxima and the following decreasing points are compared with the relative maxima minus a noise parameter. If the measured data points decrease less than the relative maxima minus the noise parameter, then the relative maxima is identified as the absolute maxima 308 of the beat. If, however, the data points do not decrease in value below the relative maxima minus the noise parameter, but instead begin to increase in magnitude again, then the relative maxima is discarded. The same noise parameter based noise determination is carried out through the case of data points with decreasing magnitude when searching for the absolute minima 310 of the beat. In this case, the dicrotic notch 312 of the waveform is neither identified as a maximum nor a minimum through an intelligent choice of the noise parameter.

The "duration" and "threshold" parameters are applied to the waveform data after at least one set of absolute minima and maxima have been determined (step 3). The minima 310 of each blood pressure beat is defined here to be the beginning of systole 314, and maximum 308 of the blood pressure beat is defined to be the peak of systole. The end of systole 316 is also defined as the beginning of diastole of the same beat. The end of diastole 314 is the beginning of systole for the next, adjacent beat. The difference in time between the beginning 314 and the peak of systole (or maximum 308) for a given beat is defined to be the duration 304 of the beat.

Since the heart and vascular system behave within certain physiological limits, the length of time that it takes for the blood pressure to rise from the beginning of systole to the peak pressure of systole must lie within some reasonable physiological range. This reasonable physiological range of rise times is defined here to be bounded by parameters of minimum duration 318 and maximum duration 320 which define the allowable duration limits for the systolic upstroke portion of any beat waveform. If the duration of systolic upstroke falls outside this defined range, then it is probably not a blood pressure beat and, therefore, most likely a motion artifact or an electrical disturbance. In this case, the waveform data corresponding to the blood pressure beat is discarded as an invalid representation of the true blood pressure beat waveform.

Similarly, the blood pressure beat waveform threshold 302 is defined to be the difference in magnitude between the beat maxima 308 and the beat minima 310 over a systolic upstroke period 304 for a given single beat waveform. Due to physiological constraints, this threshold parameter must also fall within certain physiological limits. These limits are defined by the minimum threshold limit 324 and the maximum threshold limit 322. The measured threshold 302 of the beat must fall within the minimum and maximum threshold limits for the waveform data of the blood pressure beat to be considered a valid representation of the blood pressure waveform. If the measured threshold falls outside these defined limits, the waveform data corresponding to the blood pressure beat is discarded.

The "threshold" parameter is also useful for identifying the strength of the blood pressure signal. The signals that are too weak, because for instance the sensor is improperly positioned relative to the radial artery, will not be examined further. Likewise, signals that are too large, because of for instance a motion artifact, will also not be analyzed further. These threshold and duration limits can be visualized as a rectangular region in a plane bounded by the minimum and maximum threshold and duration parameters. All good blood pressure beat waveforms must fall within the rectangular region bounded by these two sets of parameters to be considered for further processing. Upon verification of a valid beat (Step 4), the location of the beat waveform data is stored in memory along with its respective minima and maxima values (Step 5). A beat counter is then incremented and the same beat detect process is applied to the next sequential blood pressure beat data to determine its validity.

After two consecutive beats have been found then the lockout 306 parameter can be applied. Again, since the heart behaves within certain limits we do not expect two beats to occur within a certain period of time. If two beats do occur within this lockout period of time 306, then one or both must have resulted from artifact. After three consecutive beats have been found to be valid by the beat detection process, a "beat evaluation" process is applied to the validated waveform data to determine a set of parameters useful in the determination of a blood pressure measurement from the beat waveform data.

FIG. 6 shows a flowchart diagram of the main steps in the "beat evaluation" process for extracting a set of parameters from the validated blood pressure beat waveforms, and using the parameters to predict blood pressure and heart rate. The beat evaluation process begins with Step 1 by applying a moving average filter, or box car filter, to the beat data of successive beat waveforms. The moving average filter provides a low pass filter function having a 3 dB break point at approximately 11 Hz, which is given by the equation:

$$Y(I) = \sum_{J=I-2}^{I+2} \frac{X(J)}{5}$$

Next, Step 2, the first derivative of the beat data of successive beat waveforms is determined by the equation:

$$X'(I) = \frac{X(I-2) + X(I+3)}{5}$$

Next, Step 3, the time location of various waveform landmarks is determined. These landmarks include waveform maxima 308, waveform minima 310, location of the maximum slope of the waveform, and location of the dicrotic notch 312. The location of the maxima and minima are derived by identifying points at which the first derivative as defined above equals zero. An uncalibrated arithmetic mean of the beat data are also calculated. Values associated with the maxima, minima, maximum slope, dicrotic notch, and uncalibrated arithmetic mean are recorded for each beat.

The dicrotic notch 312 is a feature of the arterial pressure waveform which is caused by the closure of the aortic valve in the heart. The aortic valve closure is a passive, non-muscular event which occurs when the pressure in the aorta is greater than that in the left ventricle of the heart. The valve closes rapidly and causes a pressure disturbance in the otherwise monotonically decreasing diastolic portion of the pressure waveform. The dicrotic notch is named because, when looking at the pressure in the aorta, there is a small positive deflection in the pressure caused by the valve closure.

The dicrotic notch, as measured non-invasively in the radial artery by the piezoelectric sensor of FIG. 1, or invasively by an arterial line, is similar to that found directly within the aorta, and is also characterized by a small positive deflection in pressure. The shape of the pressure disturbance in the radial artery is affected by the condition of the arteries leading from the aorta to the radial artery. Therefore the notch may have various appearances. It is, however, always present in some form. The three most typical forms which are encountered are, (1) the standard small positive deflection like that observed in the aorta representing a true "notch" in pressure, (2) a flat waveform extending for a short period of time with very small or zero slope, perhaps a dicrotic "plateau", and (3) a decrease in the negative slope of the diastole portion of the beat waveform indicating perhaps a dicrotic slope change. These three cases can all be detected by looking for a decrease in the magnitude of the negative slope of the waveform during the diastolic portion of the beat waveform. One method employed by the preferred embodiment of the invention is to label the maximum negative slope following the peak of systole, maxima 308. When, for instance, the slope decreases to less than 50 percent of the measured maximum slope then the dicrotic notch is identified. A physiological condition that can be imposed on the detected location of the dicrotic notch is that the dicrotic notch must occur after a time period equal to the sum of the time period from the waveform minimum 310 to the waveform maxima 308 plus the time period of the dicrotic window 326. This condition may be necessary for proper detection since there are occasionally pressure reflection phenomena which occur between the peak of systole and the dicrotic notch which may be falsely identified as the dicrotic notch.

Next, there are several parameters derived from the blood pressure waveform which are of interest in determining blood pressure values from the waveform data and are calculated in Step 4. It is important to note that all of the parameters computed are independent of the waveform amplitude. This is because the amplitude of the piezoceramic sensor signal is not calibrated to an absolute pressure. Such a calibration would be dependent on many variables which are difficult to control such as skin and local artery properties, and the application force with which the sensor is pressed against the skin. It should be noted that all of the parameters presented here are either ratios of waveform amplitudes or times of waveform events.

The first computed parameter is called the Compensated Dicrotic Ratio (CDR). The CDR is the product of two components. The first component of the CDR is called the Dicrotic Ratio (DR) and is defined as the ratio between the height of the dicrotic notch and the height of the systolic peak. The first component is defined mathematically:

DR=[S(dicrotic)−S(begin systole)/(S(peak systole)−S(begin systole)]

where S stands for the signal that results from the piezoceramic sensor and the signal processing described above, S(dicrotic) is the value of this signal at the dicrotic notch and similarly for S(begin systole) and S(peak systole) at those times.

The other component of the CDR is the filling time component (FTC). The filling time is defined to be the length of time that the heart takes to fill with blood before the heart muscle contracts and can be approximated as the length of time from when the aortic valve closes until it reopens. This length of time is identified on the blood pressure beats as the time from the dicrotic notch of the previous beat to the start of systole of the current beat, i.e., diastole of FIG. 4. The FTC of the CDR is defined as:

FTC=1/[(previous beat dicrotic time 316)-(current beat beginning of systole time 314)].

The FTC compensates the DR for the effect of filling time. A long filling time would mean that the reference point for the DR, i.e., S(begin systole), would have a smaller value since the signal is decreasing in diastole. Making the reference point smaller would tend to make the DR larger and this is offset by dividing by the larger filling time in the CDR.

The second parameter is the Beat Time Ratio (BTR) which examines the ratio between the time spent in systole and the time spent in diastole. This is defined as:

BTR=[(dicrotic time)-(begin systole time)]/[(end diastole time)-(dicrotic time)]

The third parameter is the Beat Mean Ratio (BMR) which examines the relation between the mean value of the sensor signal in systole to that in diastole. This is defined as:

BMR=M(begin systole . . . dicrotic)/M(dicrotic . . . end diastole)

where M(begin systole . . . dicrotic) is the mean S signal value between the time of the beginning of systole and the time of the dicrotic notch and likewise for the M(dicrotic . . . end diastole). The mean M is the integral of the signal S over the time period divided by the length of the time period.

The fourth parameter is the RC Time Constant (RCTC). One representation of the arterial system models the peripheral arteries and capillaries as a parallel combination of a resistor (R) and a capacitor (C). The resistor represents the resistance of these peripheral vessels and the capacitor represents the compliance of the arteries. The response of the model from a pulse input is a decaying exponential after the input has stopped. The blood pressure signal in diastole can be modeled as this single exponential. A single exponential is fit to the diastolic portion of the sensor signal and the RCTC is defined to be the time constant of this exponential. This is defined as:

S(peak dicrotic . . . end diastole)=A exp(-t/RCTC)

where S(peak dicrotic . . . end diastole) is the sensor signal between these two times, A is a constant which is ignored and t is time. To save on computation time the exponential is derived from only the peak dicrotic point and an intermediate diastolic point.

In step 5 the mean arterial blood pressure MAP and heart rate "HR" are predicted from the above parameters computed from the sensor waveform and displayed. The MAP is computed using a constant coefficient equation of the parameters. The equation was determined to be:

MAP=a CDR$^2$+b BTR+c BMR+D RCTC+e FTC+k where a,b,c,d,e and k are the constant coefficients. The coefficients are determined by performing a multiple polynomial regression between the sensor signal parameters and a known MAP from an invasive catheter. A large number of blood pressure beats from a wide range of patients with a wide range of blood pressures were examined. The correlation was validated by predicting blood pressures within an acceptable margin of error.

A typical range of values for the coefficients is shown in Table I below:

TABLE I

| | | Upper | Lower |
| --- | --- | --- | --- |
| a | CDR$^2$ | 52.9 | 44.1 |
| b | BTR | −34.8 | −68.5 |
| c | BMR | 2.19 | 0 |
| d | RCTC | −.6 | −16.8 |
| e | FTC | 21.4 | 11.8 |
| k | Constant | 84.8 | 71.8 |

The heart rate HR is computed by first measuring the difference in time between the start of systole 314 of the current beat and the start of systole 314 of the following beat. The heart rate is defined to be the reciprocal of this time difference, or mathematically:

HR=1/{(time of systole 314 of next beat) - (time of systole 314 of current beat)}

In step 5 after the mean arterial pressure MAP and heart rate HR are calculated, they are displayed and/or recorded.

Equivalents

Those skilled in the art will know, or be able to ascertain using no more than routine experimentation, many equivalents to the specific embodiments of the invention described herein.

These and all other equivalents are intended to be encompassed by the following claims:

We claim:

1. A non-invasive blood pressure monitoring systems comprising:
   a) a transducer means including a piezoelectric element responsive to displacement of a transfer member located on a body portion adjacent a radial artery wall for detecting displacement of said radial artery wall caused by blood pressure pulses and generating an electrical displacement signal in response thereto;
   b) a signal processor means for receiving said displacement signal and converting the displacement signal to an electrical analog blood pressure waveform signal;
   c) computer means for extracting blood pressure parameters and physiological measurements from said waveform signal by recognizing certain patterns in the waveform of the waveform signal; and
   d) display means for displaying said parameters, measurements and waveform signal, and wherein said computer means calculates a compensated dicrotic notch ratio CDR by determining the product of a dicrotic ratio DR and a filling time component FTC.

2. The system of claim 1 in which the computer means also calculates a beat time ratio BTR which is the ratio of a time spent in systole to a time spent in diastole.

3. The system of claim 2 in which the computer means calculates a beat ratio BMR which is a ratio of a mean value of the waveform signal between a beginning of systole and an occurrence of a dicrotic notch and the occurrence of the dicrotic notch and an end of diastole.

4. The system of claim 3 in which the computer means calculates an RC time constant RCTC which is an experimental factor representing said waveform signal between the occurrence of a peak dicrotic and an end of diastole.

5. The system of claim 4 in which the computer means includes means for calculating a mean arterial blood pressure MAP from the equation:

$$MAP = a CDR^2 + bBTR + cBMR + dRCTC + eFTC + k$$

wherein a, b, c, d, e, & k are constants empirically determined by clinical evaluation.

6. A method of non-invasive blood pressure monitoring comprising the steps of:
   a) detecting displacement of a radial artery caused by blood pressure pulses and generating an electrical displacement signal in response thereto using a piezoelectric sensor having a displacement transfer member;
   b) converting the displacement signal to an analog blood pressure waveform signal; and
   c) extracting blood pressure parameters and physiological measurements from said waveform signal by recognizing predetermined patterns in the waveform based upon empirical data obtained from clinical studies and wherein one such extracted parameter is a compensated dicrotic notch ratio CDR which is determined by calculating the product of a dicrotic notch ratio DR and a fill time component FTC.

7. The method of claim 6 in which another extracted parameter is the beat time ratio BTR which is the ratio of a time spent in systole to a time spent in diastole.

8. The method of claim 7 in which another extracted parameter is a beat mean ratio BMR which is the ratio of a mean value of the waveform signal between a beginning of systole and an occurrence of a dicrotic notch and the occurrence of the dicrotic notch and an end of diastole.

9. The method of claim 8 in which another extracted parameter is an RC time constant RCTC which is an experimental factor representing the waveform signal between the occurrence of a peak dicrotic to an end of diastole.

10. The method of claim 9 in which a mean arterial blood pressure MAP is calculated from the equation:

$$MAP = a CDR^2 + bBTR + cBMR + dRCTC + eFTC + k$$

wherein a, b, c, d, e, & k are constants empirically determined by clinical evaluation.

11. A blood pressure monitoring system comprising:
   a) means for external application to a living body including a piezoelectric element responsive to displacement of a transfer member contacting a body portion adjacent a radial artery wall for generating an electrical digital blood pressure waveform signal in response to displacements of said radial artery wall caused by fluctuations in instantaneous blood pressure within the body;
   b) computer means for extracting blood pressure parameters and physiological measurements from said digital signal and measuring the height of the waveform signal and recognizing certain patterns in the waveform of the waveform signal; and
   c) display means for displaying said parameters, measurements and waveform signal; and wherein the computer means calculates a beat time ratio BTR which is the ratio of a time spent in systole to a time spent in diastole.

12. The system of claim 11 in which the computer means calculates a beat time ration BTR which is the ratio of a time spent in systole to a time spent in diastole.

13. The system of claim 12 in which the computer calculates a beat ratio BMR which is a ratio of a mean value of the waveform signal between a beginning of systole and an occurrence of a dicrotic notch and the occurrence of the dicrotic notch and an end of diastole.

14. The system of claim 13 in which the computer means calculates an RC time constant RCTC which is an experimental factor representing the waveform signal between the occurrence of a peak dicrotic and the end of diastole.

15. The system of claim 14 in which the computer means includes means for calculating a mean arterial blood pressure MAP from the equation:

$$MAP = a CDR^2 + bBTR + cBMR + dRCTC + eFTC + k$$

wherein a, b, c, d, e, & k are constants empirically determined by clinical evaluation.

16. A method of blood pressure monitoring comprising the steps of:
   a) detecting displacement of a radial artery wall caused by blood pressure pulses and generating a displacement signal using a piezoelectric sensor having a displacement transfer member;
   b) generating an analog blood pressure waveform signal from said displacement signal;
   c) converting the analog waveform signal to a digital signal;
   d) extracting blood pressure parameters and physiological measurements from said digital signal by recognizing predetermined patterns in the waveform based upon empirical data obtained from clinical studies and in which an extracted blood pressure parameter is a compensated dicrotic notch ratio CDR which is determined by calculating the product of a dicrotic ratio DR and a fill time component FTC.

17. The method of claim 16 in which an extracted parameter is a beat time ratio BTR which is the ratio of a time spent in systole to a time spent in diastole.

18. The method of claim 17 in which an extracted parameter is a beat mean ratio BMR which is the ratio of a mean value of the waveform signal between a beginning of systole and an occurrence of a dicrotic notch and the occurrence of the dicrotic notch and an end of diastole.

19. The method of claim 18 in which an extracted parameter is an RC time constant RCTC which is an experimental factor representing the waveform signal between an occurrence of a peak dicrotic to the end of diastole.

20. The method of claim 19 in which a mean arterial blood pressure MAP is calculated from the equation:

$$MAP = \frac{a}{CDR^2} + bBTR + cBMR + dRCTC + eFTC + k$$

wherein a, b, c, d, e, & k are constants empirically determined by clinical evaluation.

21. A non-invasive blood pressure sensing system comprising:
   a) a transducer comprised of a piezoceramic element having a housing and attachable to the wrist of a patient by a disposable and removable adhesive, the element being responsive to displacement of a transfer member disposed adjacent a radial artery for detecting displacement of the radial artery caused by blood pressure pulses and generating an electrical displacement signal in response thereto;
   b) a signal processor means for receiving said displacement signal and converting the displacement signal to an electrical blood pressure waveform signal;
   c) computer means for receiving the blood pressure waveform signal and extracting blood pressure parameters and physiological measurements from said waveform signal by recognizing certain patterns in the waveform of the waveform signal and wherein said parameters include the following:
      a compensated dicrotic notch ratio CDR, a beat time ratio BTR, a beat mean ratio BMR, a RC time constant RCTC; and
   d) display means for displaying said parameters, measurements and waveform signal.

22. The system of claim 21 in which the computer means includes a means for calculating a mean arterial blood pressure MAP from the equation:

$$MAP = \frac{a}{CDR^2} + bBTR + cBMR + dRCTC + eFTC + k$$

wherein a, b, c, d, e, & k are constants empirically determined by clinical evaluation.

* * * * *